United States Patent [19]

Kobayashi

[11] Patent Number: 4,682,504

[45] Date of Patent: Jul. 28, 1987

[54] DEVICE FOR MEASURING A STIFFNESS OF A GOLF-CLUB SHAFT

[75] Inventor: Masashi Kobayashi, Matsudo, Japan

[73] Assignee: Maruman Golf Co., Ltd., Tokyo, Japan

[21] Appl. No.: 890,589

[22] Filed: Jul. 30, 1986

[30] Foreign Application Priority Data

Jul. 31, 1985 [JP] Japan .................. 60-167421

[51] Int. Cl.$^4$ ............................ G01N 3/20; G01N 3/00
[52] U.S. Cl. ............................................ 73/854; 73/794
[58] Field of Search ................ 73/794, 788, 795, 847, 73/849, 854; 273/80 R, 80 B, 77 A, 77 R, 186 R, 186 A

[56] References Cited

U.S. PATENT DOCUMENTS

| | | | |
|---|---|---|---|
| 2,351,574 | 6/1944 | Siversten | 73/847 |
| 4,319,750 | 3/1982 | Roy | 273/DIG. 23 |
| 4,431,187 | 2/1984 | Rumble et al. | 273/80 R |
| 4,517,843 | 5/1985 | Leger | 73/847 |
| 4,558,863 | 12/1985 | Haas et al. | 273/80 B |
| 4,591,157 | 5/1986 | Parente et al. | 273/80 B |

*Primary Examiner*—Stewart J. Levy
*Assistant Examiner*—Robert R. Raevis
*Attorney, Agent, or Firm*—Armstrong, Nikaido, Marmelstein & Kubovcik

[57] ABSTRACT

A device for measuring a stiffness of a golf-club shaft comprises a clamp for holding one end of a golf-club shaft so that the golf-club shaft extends in a substantially horizontal position. A pointer member having a tip end and a root portion is detachably attached at the root portion thereof to the other end of the golf-club shaft held by the clamp so that the pointer member extends in a substantially horizontal position perpendicular to a longitudinal axis of the golf-club shaft. A counterweight is detachably attached to the tip end of the pointer member and applies a predetermined flexure and torsion load to the golf-club shaft through the pointer member. A vertical displacement measuring instrument is provided to measure the amount of vertical displacement of the tip end of the pointer member produced by torsion and flexure of the golf-club shaft when the predetermined load of the counterweight is applied to the golf-club shaft through the pointer member.

8 Claims, 8 Drawing Figures

DEVICE FOR MEASURING A STIFFNESS OF A GOLF-CLUB SHAFT

BACKGROUND OF THE INVENTION

1. Field of the Invention

The present invention relates to a device for measuring a stiffness of a golf-club shaft and, more particularly, to a device for directly measuring a stiffness of the club shaft, which is a combination of flexure strength and torsion strength.

2. Description of the Related Art

Generally, a golf-club shaft is subjected to flexure and torsion when swung during play or practice. A golf player feels the degree of flexure and torsion as a shaft stiffness. A club shaft having small flexure and torsion has a stiff feel, and a club shaft having large flexure and torsion has a soft feel. Generally, a player having a strong swing can move a club shaft at a high head speed, and thus a stiffer club shaft, i.e., a shaft having small flexure and torsion, is more suitable for such a player. A player with a weak swing, however, moves a club shaft at a low head speed, and thus a softer shaft, i.e., a shaft having large flexure and torsion is more suitable for such a player.

Conventionally, a device for measuring only a flexure strength of a golf-club shaft has been proposed and used, and a device for measuring only a torsion strength of a golf-club shaft also has been proposed and used. Accordingly, to inspect a stiffness of a golf-club shaft, it has been necessary to separately measure the flexure strength and torsion strength of a club shaft by using two different devices and to estimate a stiffness of the shaft based on the measurement values. Consequently, there is a demand for a method of directly measuring a stiffness of a golf-club shaft.

SUMMARY OF THE INVENTION

According to the present invention, there is provided a device for measuring a stiffness of a golf-club shaft, comprising: a clamp for holding one end of a golf-club shaft so that the golf-club shaft extends substantially horizontal from the one end to the other end thereof; a pointer member having a tip end and a root portion detachably attached to the other end portion of the golf-club shaft held by the clamp so that the pointer member extends substantially horizontal from the root portion to the tip end thereof perpendicular to a longitudinal axis of the golf-club shaft; a counterweight detachably attached to the tip end of the pointer member for supplying a predetermined flexure and torsion load to the golf-club shaft through the pointer member; and a vertical displacement measuring means for measuring the amount of a vertical displacement of the tip end of the pointer member produced by a torsion and flexure of the golf-club shaft when the predetermined load of the counterweight is supplied to the golf-club shaft through the pointer member. The vertical displacement measuring means preferably includes a measuring column having a vertical scale.

According to the above-mentioned device of the present invention, when the counterweight is attached to the tip end of the pointer member, the golf-club shaft is simultaneously subjected to flexure and torsion and thus is deformed and moves the tip end of the pointer member in the vertical and horizontal directions. The amount of vertical displacement of the tip end of the pointer member is directly proportional to a degree of deformation of the shaft as a combination of shaft flexure and torsion, and a degree of such deformation of the shaft corresponds to a degree of the shaft stiffness felt by a player while swinging the golf club. Consequently, the stiffness of the golf-club shaft can be directly inspected by measuring the amount of vertical displacement of the tip end of the pointer member of the device according to the present invention.

Preferably, the device for measuring a stiffness of the golf-club shaft further comprises a torsion measuring means for measuring a degree of displacement of the pointer member caused by only a torsion of the golf-club shaft. The torsion measuring means may be a leveling instrument arranged in the pointer member or may include a scale board for measuring a horizontal displacement of the tip end of the pointer member. According to this construction of the device, the single measurement operation can allow not only a measurement of the shaft stiffness but also an inspection of the relationship between the shaft torsion strength and the shaft flexure strength based on the data measured by the vertical displacement measuring means and the data measured by the torsion measuring means.

BRIEF EXPLANATION OF THE DRAWINGS

The foregoing and other objects and advantages of the present invention will be better understood from the following detailed description with reference to the preferred embodiments illustrated in the drawings; wherein.

DETAILED DESCRIPTION OF THE INVENTION

Figure 1:
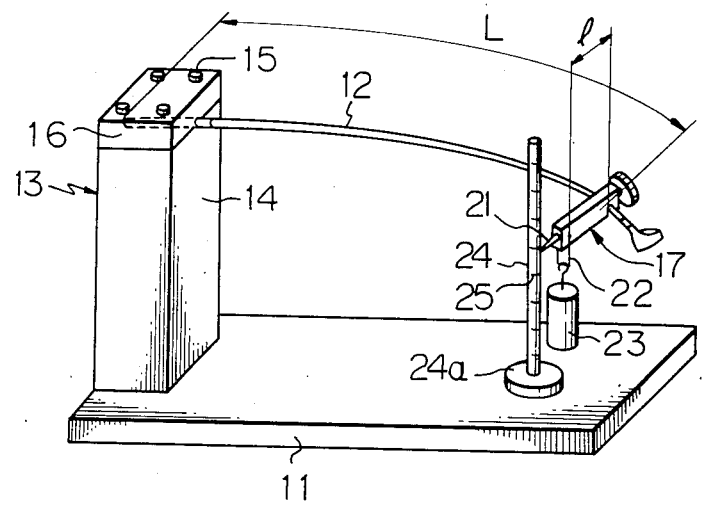
FIG. 1 is a perspective view of a device for measuring a stiffness of a golf-club shaft according to a first embodiment of the present invention.

FIGS. 1 to 4 show a device for measuring a stiffness of a golf-club shaft according to one embodiment of the present invention. Referring to FIG. 1, the device comprises a base 11, and clamp portion 13 standing at one end portion of the base 11 to hold one end (e.g., a grip end portion) of a golf-club shaft 12 is such a manner that the shaft 12 is maintained substantially in a horizontal posture. The clamp portion 13 comprises a stationary support 14 fixed to the base 11 and a holding member 16 which can be fixed to the upper surface of the stationary support 14 by bolts 15. Grooves such as V-shaped grooves are formed in the upper surface of the stationary support 14 and the lower surface of the holding member 16 to engage with the shaft 12. Therefore, the shaft 12 is fixed between the stationary support 14 and the holding member 16 by fastening the bolts 15.

Figure 4:
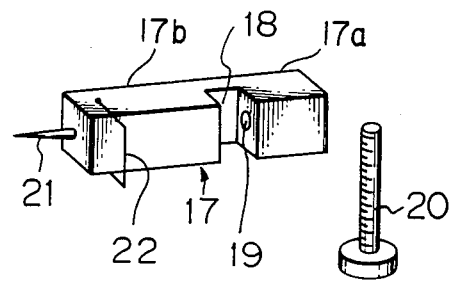
FIG. 4 is an exploded perspective view of the pointer member in the device of FIG. 1.

The device for measuring the stiffness of the golf-club shaft comprises a pointer member, generally designated 17, detachably attached to the other end portion (e.g., a shaft portion near the club head) of the shaft 12. As shown in FIG. 4, the pointer member 17 comprises a groove 18 at a root portion 17a thereof for receiving the shaft 12. The shaft 12 inserted in the groove 18 can be fixed by a bolt 20 threadably engaged in a screw hole 19 in the pointer member 17. The pointer member 17 is provided at the tip end 17b thereof with a sharpened pin 21. The pointer member 17 is approximately horizontally mounted on the shaft 12 at a position which is a predetermined distance L from the grip-side end of the shaft 12. The pointer member 17 is preferably as light as possible.

Figure 2:
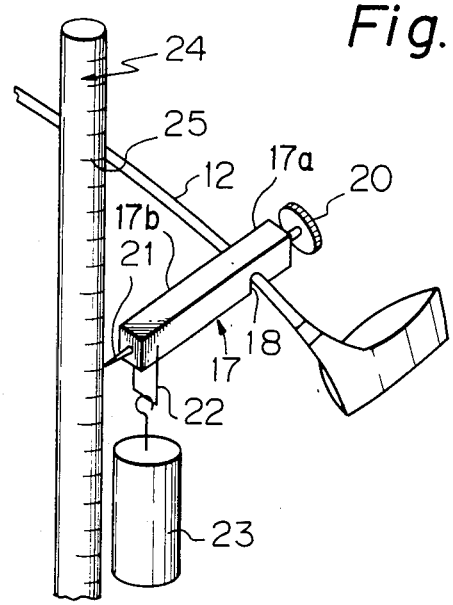
FIG. 2 is an enlarged perspective view showing the main part of the device in FIG. 1.
Figure 3:
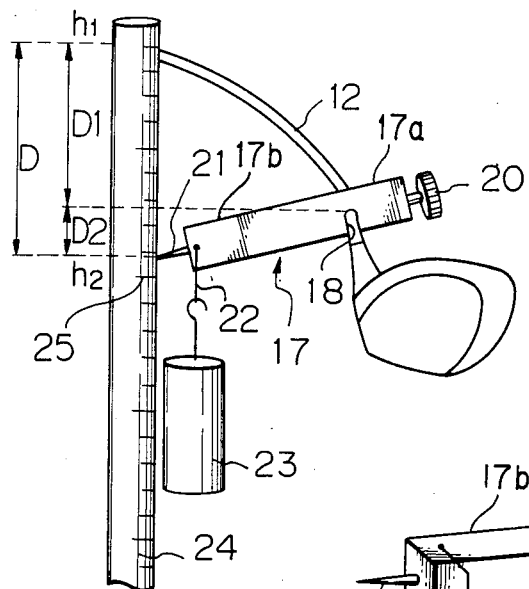
FIG. 3 is an enlarged end view showing the main part of the device in FIG. 1.

A counterweight 23 can be suspended through a hanger 22 at the tip end 17b of the pointer member 17 at a predetermined distance l from the groove 18. When the counterweight 23 is suspended at the tip end of the pointer member 17, the shaft 17 is flexed and subjected to torsion around the axis of the shaft 12. Therefore, as shown in FIGS. 2 and 3, the tip end of the pin 21 of the pointer member 17 is displaced vertically downward from an initial position upon flexure and torsion of the shaft 12.

The device for measuring the stiffness of the golf-club shaft further comprises means for measuring a vertical displacement of the tip end of the pin 21 of the pointer member 17. The vertical displacement measuring means comprises a measuring column 24 having a vertical scale 25. The measuring column 24 is arranged on the upper surface of the base 11 and is horizontally movable therealong.

In the device having the above-mentioned arrangement, in order to measure a stiffness of the golf-club shaft, the grip portion, for example, of the shaft 12 is fixed by the stationary support 14 and the holding member 16 in such a manner that the shaft 12 is maintained in a substantially horizontal position, and the shaft portion near the club head is engaged with the groove 18 in the pointer member 17 to fix the pointer member 17 to the shaft 12. A height of the tip end 17b of the pin 21 of the pointer member 17 is then measured. The height of the tip end of the pin 21 is given as h1. The counterweight 23 is then suspended from the tip end of the pointer member 17 through the hanger 22, and a height of the tip end of the pin 21 of the pointer member 17 is measured. The height of the tip end of the pin 21 is given as h2. The tip end of the pin 21 of the pointer member 17 is displaced downward by an amount D (D=h1−h2) upon the flexure and torsion imposed on the shaft 12 by suspension of the counterweight 23. As shown in FIG. 3, the amount D of the vertical displacement is the sum of an amount D1 of a downward displacement by the flexure of the shaft 12 and an amount D2 of a downward displacement by the torsion of the shaft 12. Further, the amount D of a vertical displacement of a tip end of the pin 21 is substantially inversely proportional to a degree of stiffness of the golf-club, shaft held by a player while swinging the club. According to the device of the present invention, the stiffness of the shaft 12 can be directly inspected by measuring the vertical displacement D of the tip end of the pin 21 of the pointer member 17.

Figure 5:
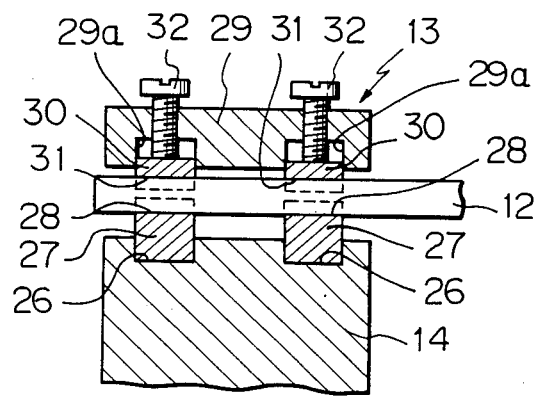
FIG. 5 is a sectional view showing a modification of a clamp portion in a device for measuring a stiffness of a golf-club shaft according to a second embodiment of the present invention.

FIG. 5 shows a main part of a device for measuring a stiffness of a gold-club shaft according to a second embodiment of the present invention. The same reference numerals as in the first embodiment shown in FIGS. 1 to 4 denote the same parts in the second embodiment shown in FIG. 5.

The second embodiment includes a modification of the clamp portion 13 in which stationary grippers 27 having V-shaped grooves 28 are detachably inserted into recesses 26 formed in the upper surface of the stationary support 14, and movable grippers 30 having V-shaped grooves 31 are detachably inserted into recesses 29a formed in the lower surface of the upper support 29 secured above the stationary support 14. A grip-side portion of the golf-club shaft 12 or an opposite side portion of the shaft 12 near the club head is inserted between the stationary grippers 27 and the movable grippers 30, and is fastened by bolts 32. In this manner, the shaft 12 can be fixed between the grippers 27 and 30 and maintained substantially horizontal in the longitudinal direction thereof. The grippers 27 an 30 can be replaced when the stiffness of a golf-club shaft 12 having a diameter different from that of the currently gripped shaft is measured. Other arrangements are the same as those in the first embodiment.

Figure 6:
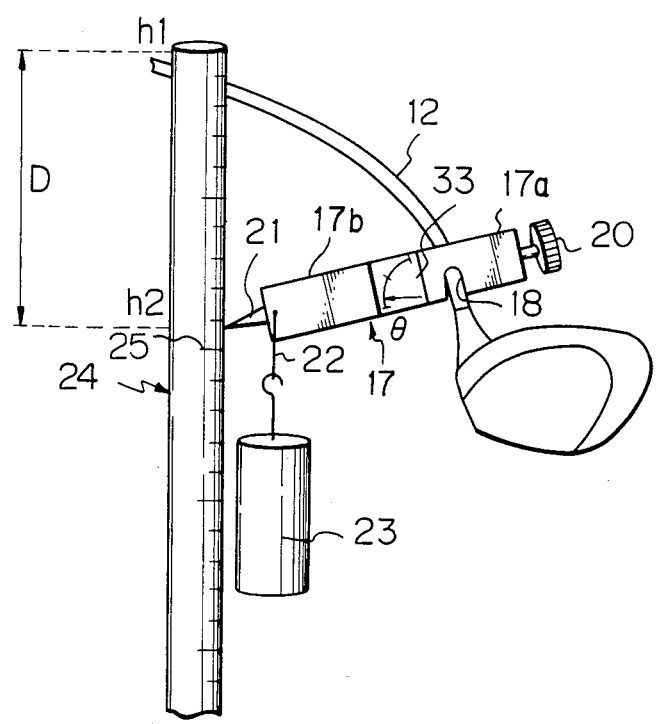
FIG. 6 is an end view showing the main part of a device for measuring a stiffness of a golf-club shaft, the device being provided with a torsion measuring means, according to a third embodiment of the present invention.

FIG. 6 shows a main part of a device for measuring a stiffness of a golf-club shaft according to a third embodiment of the present invention. The same reference numerals and characters as in the first embodiment shown in FIGS. 1 to 4 denote the same parts in the third embodiment shown in FIG. 6.

In the third embodiment, the device for measuring the stiffness of the golf-club shaft further comprises means for measuring a torsion strength of the golf-club shaft 12. The torsion strength measuring means comprises an inclination measuring instrument 33 arranged in the pointer member 17. Other arrangements are the same as those in the first embodiment.

According to the third embodiment, when the counterweight 23 is suspended from the pointer member 17, the tip end of the pin 21 of the pointer member 17 is displaced vertically downward from the initial height position and rotated downward from the initial horizontal posture. An angular displacement of the pointer member 17 is caused only by a torsion deformation of the shaft 12 upon a supply of a load of the counterweight 23. Therefore, a torsion strength of the golf-club shaft 12 can be inspected by measuring the angular displacement, i.e., an inclination angle $\theta$ of the pointer member 17. An amount D of a vertical displacement of the tip end of the pin 21 is also measured in the same manner as that in the first embodiment. Therefore, according to the third embodiment, a relationship between the torsion strength and the flexure strength of the golf-club shaft 12 can be inpected based on the relative estimation of the measured amount D of the vertical displacement of the tip end of the pin 21 and the measured inclination angle $\frac{1}{4}$ of the pointer member 17.

Among shafts having an identical stiffness, i.e., shafts indicating an identical amount of the vertical displacement of the tip end of the pin 21, a shaft having a smaller torsion strength, i.e., a shaft indicating a larger inclination angle $\theta$, is found to have a larger flexure than a shaft indicating a smaller inclination angle $\frac{1}{4}$. For example, a shaft having a large stiffness and small torsion strength is suitable for a player having a strong swing and a slow turn of the wrist, and a shaft having a large stiffness and large torsion strength is suitable for a layer having a strong swing and a fast turn of the wrist. Further, a shaft having a small stiffness and small torsion strength is suitable for a player having a weak swing and a slow turn of the wrist, and a shaft having a small stiffness and large torsion strength is suitable for a player having a weak swing and a fast turn of the wrist. According to the third embodiment of the present invention, the shafts most suitable for individual golf players can be selected based on data indicating the stiffness of the shaft and data indicating a torsion strength of the shaft.

Figure 7:
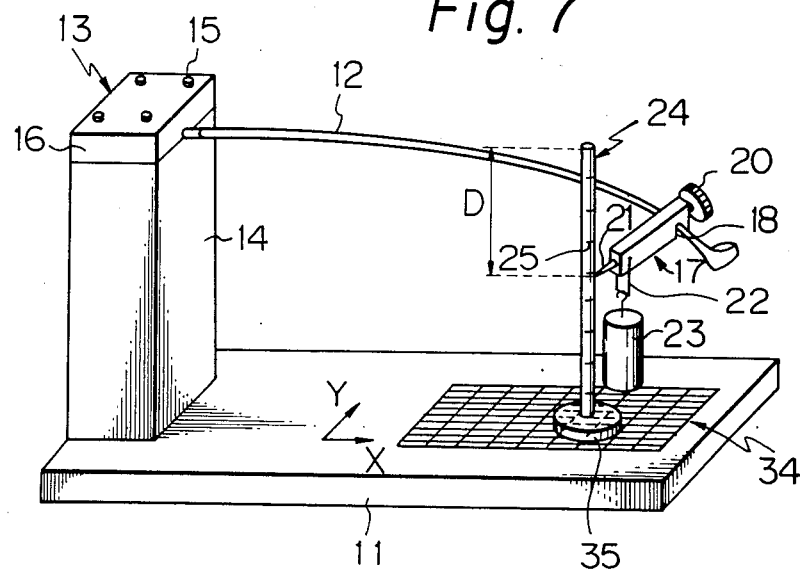
FIG. 7 is a perspective view of a device for measuring a stiffness of a golf-club shaft, the device being provided with a torsion measuring means, according to a fourth embodiment of the present invention.

FIG. 7 shows a device for measuring a stiffness of a golf-club shaft according to a fourth embodiment of the present invention. The same reference numerals and characters as in the first embodiment shown in FIGS. 1 to 4 denote the same parts in the fourth embodiment shown in FIG. 7.

In the fourth embodiment, the device for measuring the stiffness of the golf-club shaft further comprises means for measuring a torsion strength of the golf-club shaft 12. The torsion strength measuring means comprises a scale board 34 arranged on the base 11. The scale board 34 comprises X-direction scale lines extending parallel to each other along the longitudinal direction of the shaft 12 and Y-direction scale lines extending parallel to each other and perpendicular to the X-direction scale lines. A measuring column 24 is arranged on the scale board 34 and is horizontally movable therealong. The measuring column 24 is provided at the lower end thereof with a transparent bottom plate 35. The scale lines of the scale board 34 can be visually checked through the bottom plate 35. A point mark (not shown) is attached or printed at the center of the bottom plate 35 to allow reading of the position of the measuring column 24 on the scale board 34. Other arrangements are the same as those in the first embodiment shown in FIGS. 1 to 4.

According to the fourth embodiment, before a counterweight 23 is suspended from a pointer member 17, the tip end of a pin 21 of the pointer member 17 is brought into contact with the scale surface of the measuring column 24 to allow a reading of the height of the tip end of the pin 21. At the same time, the X-Y coordinates of the measuring column 24 on the scale board 34 are read at the point mark position of the bottom plate 35 of the measuring column 24. The counterweight 23 is then suspended from the pointer member 17. The tip end of the pin 21 is displaced vertically downward and horizontally in parallel to the X-Y coordinates, due to the flexure and torsion of the shaft 12. The measuring column 24 is then moved along the scale board 34 to bring the tip end of the pin 21 into contact with the scale surface of the measuring column 24. An amount D of the vertical displacement of the tip end of the pin 21 is measured in the same manner as that of the first embodiment, and an amount of the displacement of the point mark of the bottom plate 35 of the measuring column 24 in the Y-direction along the scale board 34 is measured. The displacement of the measuring column 24 in the Y-direction depends on only the torsion of the shaft 12, and the amount of the displacement thereof is inversely proportional to a degree of torsion strength of the shaft 12. Therefore, both the stiffness and torsion strength of the shaft can be simultaneously measured by the device according to the fourth embodiment.

Figure 8:
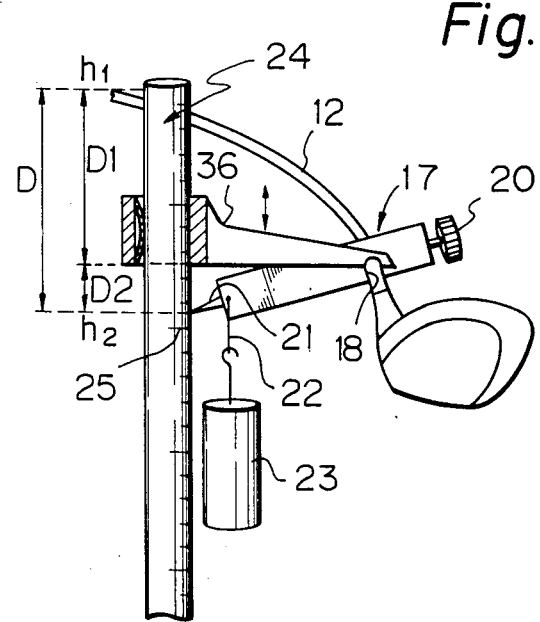
FIG. 8 is an end view showing the partial section of the main part in a device for measuring a stiffness of a golf-club shaft according to a fifth embodiment of the present invention.

FIG. 8 shows a main part of a device for measuring a stiffness of a golf-club shaft according to a fifth embodiment of the present invention. The same reference numerals and characters as in the first embodiment shown in FIGS. 1 to 4 denote the same parts in the fifth embodiment shown in FIG. 8. In the fifth embodiment, the vertical displacement measuring means comprises a measuring column 24 having a vertical scale 25, and the torsion strength measuring means comprises a measuring slider 36 which is slidably fitted to the measuring column 24 at a root portion thereof along the longitudinal direction of the column. The tip end of the measuring slider 36 can be brought into contact with the shaft 12. According to the fifth embodiment, an amount D2 of the vertical displacement of the tip end of the pin 21 depending on only a torsion of the shaft 12 can be easily measured by using the measuring slider 36, and stiffness of the shaft and the torsion strength of the shaft 12 can be simultaneously measured.

The present invention has been described with reference to the illustrated embodiments but is not limited thereto. Various changes and modifications may be made within the spirit and scope of the invention and the scope of the appended claims. For example, the displacement D may be measured and displayed by using an electric or electronic circuit with an optical or magnetic sensor. Further, the device according to the present invention also may be applied to a measurement of stiffness of a shaft for a golf-club before attaching the shaft to a club-head.

I claim:
1. A device for measuring a stiffness of a golf-club shaft, comprising:
    a clamp means for holding one end of said golf-club shaft to be measured so that when said one end of said shaft is held by said clamp means, a longitudinal axis of said shaft is located substantially perpendicular to a vertical axis of said clamp means, and the other end of said shaft remote from said clamp means is unsupported;
    a pointer member having a tip end and a root portion, said root portion being detachably attached to said golf-club shaft at a position adjacent to said unsupported end of said shaft in such a manner that when said root portion is attached to said shaft, said tip end is located substantially on a horizontal plane with said root portion thereof perpendicular to longitudinal axis of a said golf-club shaft;
    a counterweight detachably attached to said tip end of said pointer member for supplying a predetermined flexure and torsion load to said golf-club shaft through said pointer member; and
    a vertical displacement measuring means for measuring the amount of a vertical displacement of said tip end of said pointer member produced by a torsion and flexure of said golf-club shaft when said predetermined load of said counterweight is applied to said golf-club shaft through said pointer member.

2. A device according to claim 1, wherein said vertical displacement measuring means includes a measuring column having a vertical scale.

3. A device according to claim 2, wherein said measuring column is horizontally movable.

4. A device according to claim 1, further comprising torsion measuring means for measuring a degree of torsion of said golf-club shaft when said predetermined load of said counterweight is applied to said golf-club shaft through said pointer member.

5. A device according to claim 4, wherein said torsion measuring means includes an inclination measuring instrument, arranged in said pointer member, for indicating an angular displacement of said pointer member when said predetermined load of said counterweight is applied to said golf-club shaft through said pointer member.

6. A device according to claim 4, wherein said torsion measuring means includes a scale board arranged horizontally for measuring an amount of horizontal displacement of said tip end of said pointer member in a direction perpendicular to said longitudinal axis of said golf-club shaft when said predetermined load of said counterweight is applied to said golf-club shaft through said pointer member, and said vertical displacement measuring means includes a measuring column having a vertical scale, said measuring column being horizontally movable on said scale board so that it is brought into contact with said tip end of said pointer member before and after said predetermined load of said counterweight is applied to said golf-club shaft through said pointer member.

7. A device according to claim 6, wherein said scale board has a plurality of first scale lines extended in parallel to each other and to said longitudinal axis of said shaft and a plurality of second scale lines extended in parallel to each other and perpendicular to said first scale lines, and said measuring column is provided at the lower end thereof with a transparent bottom plate so that said first and second scale lines can be visually checked through said bottom plate.

8. A device according to claim 4, wherein said vertical displacement measuring means includes a measuring column having a vertical scale, and said torsion measuring means includes a measuring slider having a tip portion and root portion slidably attached to said measuring column, said tip portion of said measuring slider being formed to engage with said golf-club shaft.

* * * * *